US012272433B2

(12) United States Patent
Wren et al.

(10) Patent No.: US 12,272,433 B2
(45) Date of Patent: Apr. 8, 2025

(54) SYSTEMS AND METHODS FOR PREDICTING ADOPTION OF A THERAPY

(71) Applicant: ResMed Sensor Technologies Limited, Dublin (IE)

(72) Inventors: Michael Wren, Dublin (IE); Redmond Shouldice, Dublin (IE); Sam Coffey, Dublin (IE)

(73) Assignee: RESMED SENSOR TECHNOLOGIES LIMITED, Dublin (IE)

(*) Notice: Subject to any disclaimer, the term of this patent is extended or adjusted under 35 U.S.C. 154(b) by 388 days.

(21) Appl. No.: 17/764,772

(22) PCT Filed: Sep. 28, 2020

(86) PCT No.: PCT/IB2020/059059
§ 371 (c)(1),
(2) Date: Mar. 29, 2022

(87) PCT Pub. No.: WO2021/064551
PCT Pub. Date: Apr. 8, 2021

(65) Prior Publication Data
US 2022/0406420 A1    Dec. 22, 2022

Related U.S. Application Data
(60) Provisional application No. 62/908,528, filed on Sep. 30, 2019.

(51) Int. Cl.
*G16H 10/60* (2018.01)
*G16H 20/40* (2018.01)
(Continued)

(52) U.S. Cl.
CPC .......... *G16H 10/60* (2018.01); *G16H 20/40* (2018.01); *G16H 50/30* (2018.01); *G16H 50/20* (2018.01)

(58) Field of Classification Search
None
See application file for complete search history.

(56) References Cited

U.S. PATENT DOCUMENTS
2015/0223968 A1* 8/2015 Hervy .................. A61F 5/56
                                                 128/848
2016/0199215 A1* 7/2016 Kopelman .......... A61F 5/566
                                                 128/848
(Continued)

FOREIGN PATENT DOCUMENTS
JP    2004159888 A    6/2004
JP    2008543384 A   12/2008
(Continued)

OTHER PUBLICATIONS
Shioya et al., "Significance of nutritional rehabilitation in chronic obstructive pulmonary disease (COPD) and practice thereof", Journal of the Japan Society for Respiratory Care and Rehabilitation, Japan, Japan Society for Respiratory Care and Rehabilitation, Dec. 2011, vol. 21, No. 3, pp. 175-185 (document exemplifying well-known technique).

(Continued)

*Primary Examiner* — Ankit D Tejani
(74) *Attorney, Agent, or Firm* — NIXON PEABODY LLP (57) ABSTRACT

A system for predicting adoption of a prescribed treatment plan by an individual includes a data repository, a memory storing instruction, and a control system to execute the instructions. The data repository is communicatively coupled to a network and includes a plurality of storage devices storing data. The control system receives at least a portion of the data stored in the data repository. The at least a portion of the data is associated with the individual. The control system uses the machine learning adoption prediction algorithm to process the received at least a portion of the data to determine a likelihood that the individual will adopt (Continued)

the prescribed treatment plan. Based at least in part on (i) the prescribed treatment plan and (ii) the determined likelihood that the individual will adopt the prescribed treatment plan, the control system generates a personalized treatment adoption plan for the individual.

25 Claims, 4 Drawing Sheets

(51) Int. Cl.
*G16H 50/30* (2018.01)
*G16H 50/20* (2018.01)

(56) References Cited

U.S. PATENT DOCUMENTS

| | | | |
|---|---|---|---|
| 2017/0209657 A1 | 7/2017 | Levings et al. | |
| 2018/0303412 A1* | 10/2018 | Moore | G16H 50/20 |
| 2019/0076098 A1* | 3/2019 | Li | G16H 10/20 |

FOREIGN PATENT DOCUMENTS

| | | |
|---|---|---|
| JP | 2013252424 A | 12/2013 |
| JP | 2015526151 A | 9/2015 |
| JP | 2017501465 A | 1/2017 |
| JP | 2017523841 A | 8/2017 |
| WO | 2018/050913 A1 | 3/2018 |
| WO | 2018152366 A1 | 8/2018 |

OTHER PUBLICATIONS

Kogure et al., "Effects on sleep of sleeping with the back of the bed raised", Clinical Neurophysiology, Japan, Japanese Society of Clinical Neurophysiology, 2013, vol. 41, No. 6, pp. 505-510 (document exemplifying well-known technique).

International Search Report in International Patent Application No. PCT/IB2020/059059 mailed Feb. 11, 2021 (6 pp.).

Written Opinion in International Patent Application No. PCT/IB2020/059059 mailed Feb. 11, 2021 (12 pp.).

* cited by examiner

SYSTEMS AND METHODS FOR PREDICTING ADOPTION OF A THERAPY

CROSS-REFERENCE TO RELATED APPLICATION

This application is a U.S. National Stage of International Application No. PCT/IB2020/059059, filed Sep. 28, 2020, which claims the benefit of, and priority to, U.S. Provisional Patent Application No. 62/908,528, filed on Sep. 30, 2019, which is hereby incorporated by reference herein in its entirety.

TECHNICAL FIELD

The present disclosure relates generally to systems and methods for predicting a likelihood of an individual modifying his or her personal behavior for health benefits; specifically, the present disclosure relates to predicting a likelihood an individual will adopt a prescribed treatment plan.

BACKGROUND

Treatment plans for individuals are developed and prescribed by medical professionals (e.g., doctors, nurses, care providers, etc.) for individuals (e.g., patients) every day. However, in a number of instances, the individual fails to adopt the prescribed treatment plan or fails to adopt the complete treatment plan as prescribed. The non-adoption of prescribed treatment plans can occur due to a variety of reasons. For example, the prescribed treatment plan may involve a therapy using a device that is difficult for the individual use. For another example, the prescribed treatment plan may involve the taking of a drug that has side effects that the individual does not like or cannot handle. For another example, the prescribed treatment plan may involve a surgical procedure the individual does not want to endure. The present disclosure is directed to solving these and other problems.

SUMMARY

According to some implementations of the present disclosure, a method includes receiving data associated with an individual. A machine learning adoption prediction algorithm is used to process at least a portion of the received data to determine a likelihood that the individual will adopt a prescribed treatment plan. Based at least in part on (i) the prescribed treatment plan and (ii) the determined likelihood that the individual will adopt the prescribed treatment plan, a personalized treatment adoption plan is generated for the individual.

According to some implementations of the present disclosure, a system for predicting adoption of a prescribed treatment plan by an individual includes a data repository, a memory, and a control system. The data repository is communicatively coupled to a network and includes a plurality of storage devices storing data. The memory stores machine-readable instructions and a machine learning adoption prediction algorithm. The control system includes one or more processors and is configured to execute the machine-readable instructions to receive at least a portion of the data stored in the data repository. The at least a portion of the data is associated with the individual. The control system uses the machine learning adoption prediction algorithm to process the received at least a portion of the data to determine a likelihood that the individual will adopt the prescribed treatment plan. Based at least in part on (i) the prescribed treatment plan and (ii) the determined likelihood that the individual will adopt the prescribed treatment plan, the control system generates a personalized treatment adoption plan for the individual.

According to some implementations of the present disclosure, a method for predicting adoption of a prescribed treatment plan by an individual includes receiving at least a portion of data stored in a data repository. The at least a portion of the data is associated with the individual. The data repository is communicatively coupled to a network and including a plurality of storage devices storing the data. A likelihood that the individual will adopt the prescribed treatment plan is determined using a machine learning adoption prediction algorithm that processes the received at least a portion of the data. A personalized treatment adoption plan is generated for the individual based at least in part on (i) the prescribed treatment plan and (ii) the determined likelihood that the individual will adopt the prescribed treatment plan.

According to some implementations of the present disclosure, a system includes a data repository, a memory, and a control system. The memory stores machine-readable instructions and a machine learning adoption prediction algorithm. The control system includes one or more processors configured to execute the machine-readable instructions to accumulate the data. The data includes historical data and current data. The historical data is associated with a plurality of adopters of one or more treatment plans. The current data is associated with an individual. The control system trains the machine learning adoption prediction algorithm with the historical data such that the machine learning adoption prediction algorithm is configured to (i) receive as an input at least a portion of the current data and a prescribed treatment plan for the individual and (ii) determine as an output a likelihood that the individual will adopt the prescribed treatment plan.

The above summary is not intended to represent each implementation or every aspect of the present disclosure. Additional features and benefits of the present disclosure are apparent from the detailed description and figures set forth below.

While the present disclosure is susceptible to various modifications and alternative forms, specific implementations thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

A prescribed treatment plan is what a doctor (or the like) says an individual (e.g., a user of, for example, a CPAP device, a patient, etc.) needs as the best course of treatment. The present disclosure processes data stored in a data repository using a machine learning adoption prediction algorithm to predict how likely the individual is to adopt the prescribed treatment plan. A personalized treatment adoption plan is generated based on the determined likelihood. If it is determined that the individual is, for example, 80% or more likely to adopt the prescribed treatment plan, then the personalized treatment adoption plan can be the prescribed treatment plan. However, if it is determined that the individual is less than, for example, 80% likely to adopt the prescribed treatment plan, then the personalized treatment adoption plan can be developed to be different than the prescribed treatment plan (e.g., one or more modifications to the prescribed treatment plan).

For example, if the individual is 20% or less likely to adopt a prescribed treatment plan that prescribes use of a CPAP device at a first range of pressures (e.g., between 12 cmH2O and 16 cmH2O), then a personalized treatment adoption plan can be created that starts the individual out by having the individual use a mandibular repositioning device (MRD), then start the individual on a CPAP device at second range of pressures (e.g., where the second range of pressures is less than the first range of pressures), and then work up the CPAP device pressures to the prescribed treatment plan over time.

Figure 1:
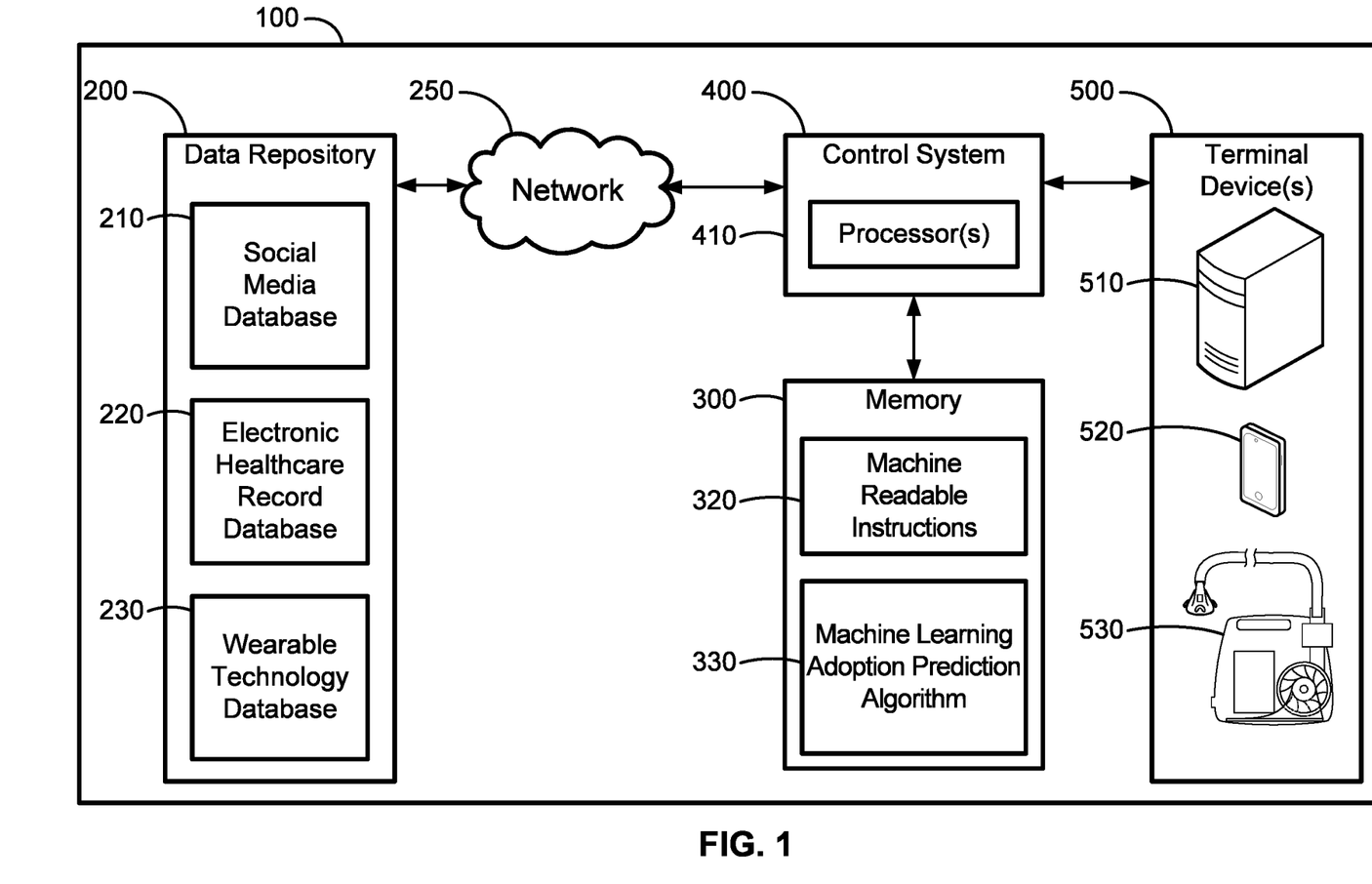
FIG. 1 is a block diagram of a system for predicting a likelihood an individual will adopt a prescribed treatment plan, according to some implementations of the present disclosure.

Referring to FIG. 1, a system 100 includes a data repository 200, a memory 300, a control system 400, and one or more terminal devices 500 (hereinafter, terminal device 500). As described herein, the system 100 generally can be used for predicting adoption, by an individual (e.g., a patient) of a prescribed treatment plan (e.g., by a doctor/prescriber). In some implementations, when the system 100 determines that an individual is not likely to adopt the prescribed treatment plan (e.g., a determined likelihood falls below a predetermined threshold), the system 100 can develop and/or suggest one or more modifications to the prescribe treatment plan in an effort to ease the individual into treatment. In such implementations, the goal of the one or more modifications is to eventually get the individual to adopt the prescribe treatment plan without modification(s). The modified prescribed treatment plan is referred to herein as a personalized treatment adoption plan. While the system 100 is shown as including various elements, the system 100 can include any portion and/or subset of the elements shown and described herein and/or the system 100 can include one or more additional elements not specifically shown in FIG. 1.

The data repository 200 is communicatively coupled to a network 250. In some implementations, the data repository 200 is communicatively connected via the network 250 to the control system 400 and/or to one or more of the terminal devices 500.

The data repository 200 includes a plurality of storage devices storing data. In some implementations of the present disclosure, the data repository 200 includes a social media database 210, an electronic healthcare record database 220, a wearable technology database 230, or any combination thereof. While the data repository 200 is shown as include various storage devices, the data repository 200 can include any subset of the elements shown and described herein and/or the data repository 200 can include one or more additional elements not specifically shown in FIG. 1.

The data stored in the data repository 200 can include a wide variety of types and/or contents of data. For example, in some implementations, the data stored in the data repository 200 includes personal data associated with multiple individuals. For another example, in some implementations, the data includes adherence data associated with multiple individuals that are similar to the individual. For another example, in some implementations, the data includes a summary of historical events that led the individual to a sleep-related diagnosis. For another example, in some implementations, the data includes an indication of a type of person that provided the individual with a sleep-related diagnosis. For another example, in some implementations, the data includes a determination of whether the individual encounters difficulties breathing during sleep. For another example, in some implementations, the data includes relationship information of the individual. For another example, in some implementations, the data includes web searches performed by the individual. For another example, in some implementations, the data includes a determination of whether the individual is likely to exhibit binge-like behavior, a determination of whether the individual is likely to change behavior, or both. For another example, in some implementations, the data includes a summary of at least a portion of a historical account of clinical behavior that the individual has changed. For another example, in some implementations, the data includes one or more daily health assessments that include the occurrence and/or frequency of headaches and/or migraines experiences by the individual. For another example, in some implementations, the data includes dependent-family information of the individual. For another example, in some implementations, the data includes subscriptions of the individual in mobile-based or web-based health applications, social media information associated with the individual, support group information related to respiration device usage, or any combination thereof. For another example, in some implementations, the data includes a determination of a tendency of the individual to be an early adopter of technology. For another example, in some implementations, the data includes treatment plans prescribed to the individual. For another example, in some implementations, the data includes information associated with whether the individual is a drug user, information associated with whether the individual consumes alcohol, or any combination thereof. It is understood the data stored in the data repository 200 can include any combination of the above described types of data and/or other types of data not specifically described herein. For another example, in some implementations, the data includes information such as age, gender, BMI, health information, whether the individual is a smoker or a non-smoker, whether the individual drinks alcohol, or any combination thereof. For another example, in some implementations, the data includes information such as self-reported pain points such as daytime drowsiness, snoring, fatigue, exercise level (duration, intensity, type), difficulties staying asleep, etc., or any combination thereof.

The data stored in the data repository 200 can include training data that is associated with a plurality of individuals. In some such implementations, the control system 400 executes machine-readable instructions (stored in the memory 300 or a different memory or both) to train a machine learning adoption prediction algorithm 330 (stored in the memory 300 or a different memory or both) with the training data. By using the training data, the machine learning adoption prediction algorithm 330 is configured to receive as an input at least a portion of the data stored in the data repository 200 that is associated with an individual and determine as an output the likelihood that the individual will adopt a prescribed treatment plan. As described herein, based on the determined likelihood of adoption by the individual, the prescribed treatment plan can be implemented or one or more aspects of the prescribed treatment plan can be modified such that a personalized treatment adoption plan is determined for the individual.

In some implementations, the control system 400 executes the machine-readable instructions 320 to receive feedback associated with a level of compliance of the individual with the prescribed treatment plan and/or the personalized treatment adoption plan. The control system 400 is further configured to generate a second personalized treatment adoption plan for the individual based at least in part on the prescribed treatment plan, a first personalized treatment adoption plan, the feedback, or any combination thereof. The feedback can include, for example, answers to one or more questions by the individual, data generated by one or more sensors, or both. In some such implementations, the one or more sensors can include a flow sensor and/or pressure sensor in a CPAP device/respiratory therapy device, a microphone in a mobile device, a motion sensor, an activity sensor (e.g., to measure activity levels of an individual like steps, etc.), a sonar sensor, an ultra-wide band radio frequency sensor, an RF sensor, a temperature sensor to measure a core and/or surface temperature of an individual and/or an ambient temperature, an audio or flow sensor to monitor snoring, or any combination thereof. The one or more sensors can be included in a wearable device worn by the individual, in one or more stationary devices in a living area of the individual, or a combination thereof.

In some implementations of the present disclosure, the received feedback is used by the machine learning adoption prediction algorithm 330 to learn from mistakes that the machine learning adoption prediction algorithm 330 makes in order to improve the performance of the system 100. For example, in one instance, the machine learning adoption prediction algorithm 330 may have predicted that an individual is 90 percent likely to adopt, but in fact learns via feedback (manually input or automatically determined) that the individual never adopted the prescribed treatment plan. In such an example, the machine learning adoption prediction algorithm 330 can be tweaked such that in future examples, the machine learning adoption prediction algorithm 330 is more likely to reduce the relative percentage likelihood, which may result in a different outcome (e.g., instead of prescribing the individual with the prescribed treatment plan, a personalized treatment adoption plan can be created).

The one or more terminal devices 500 can be associated with the individual and be configured to receive one or more notifications from the control system 400. In some implementations, the notification is based on a generated personalized treatment adoption plan for the individual. The one or more terminal devices 500 can include a personal computer 510, a mobile device 520, a respiratory therapy device 530 such as a CPAP device, or any combination thereof.

In some implementations where the system 100 includes the respiratory therapy device 530, the notification received from the control system 400 can include a command and/or instructions that cause one or more settings on the respiratory therapy device 530 to be adjusted. For example, a pressure setting or a range of prescribed pressures for the respiratory therapy device 530 can be modified to provide higher and/or lower pressures during use of the respiratory therapy device 530. The modifications to the respiratory therapy device 530 can be based at least in part on the personalized treatment adoption plan, feedback from the individual during implementation of the personalized treatment adoption plan and/or a prescribed treatment plan, a portion of the data stored in the data repository 200, or any combination thereof. While the one or more terminal devices 500 are shown as include various terminal devices, the one or more terminal devices 500 can include any subset of the elements shown and described herein and/or the one or more terminal devices 500 can include one or more additional elements not specifically shown in FIG. 1.

In some implementations, the memory 300 stores the machine-readable instructions 320 and the machine learning adoption prediction algorithm 330. The control system 400 is communicatively coupled to the memory 300. The memory 300 can include one or more physically separate memory devices, such that one or more memory devices can be coupled to and/or built into any one of the terminal devices 500. In some implementations, the memory 300 includes non-volatile memory, battery powered static RAM, volatile RAM, EEPROM memory, NAND flash memory, or any combination thereof. In some implementations, the memory 300 is a removable form of memory (e.g., a memory card).

The control system 400 includes one or more processors 410 (hereinafter, processor 410). The control system 400 is generally used to control (e.g., actuate) the various components of the system 100 and/or analyze data obtained and/or generated by the components of the system 100. The processor 410 executes machine readable instructions 320 that are stored in the memory device 300 and can be a general or special purpose processor or microprocessor. While one processor 410 is shown in FIG. 1, the control system 400 can include any suitable number of processors (e.g., one processor, two processors, five processors, ten processors, etc.). The memory 300 can be any suitable computer readable storage device or media, such as, for example, a random or serial access memory device, a hard drive, a solid state drive, a flash memory device, etc. The control system 400 and/or the memory 300 can be coupled to and/or positioned within a housing of one or more of the terminal devices 500. The control system 400 and/or the memory 300 can be centralized (within one housing) or decentralized (within two or more physically distinct housings).

In some implementations, the control system 400 is a dedicated electronic circuit. In some implementations, the control system 400 is an application-specific integrated circuit. In some implementations, the control system 400 includes discrete electronic components. The control system 400 is able to receive input(s) (e.g., signals, generated data, instructions, etc.) from any of the other elements of the system 100. The control system 400 is able to provide output signal(s) to cause one or more actions to occur in the system 100. In some implementations, the control system 400 or a portion thereof (e.g., at least one processor of the control system 400) can be located in a cloud (e.g., integrated in a server, integrated in an Internet of Things (IoT) device, connected to the cloud, be subject to edge cloud processing, etc.), located in one or more servers (e.g., remote servers, local servers, etc.), or any combination thereof.

In some implementations of the present disclosure, the processor 410 is configured to execute the machine-readable instructions 320 to receive at least a portion of the data stored in the data repository 200. In some such implementations, the portion of the data received is associated with the individual. The machine learning adoption prediction algorithm 330 is used to process the received data or a portion thereof to determine a likelihood that the individual will adopt the prescribed treatment plan. In some implementations, when determined likelihood for adoption is below a threshold value (e.g., below 95% likelihood to adopt the prescribed treatment plan, below 90% likelihood to adopt the prescribed treatment plan, below 80% likelihood to adopt the prescribed treatment plan, etc.), the processor 410 is executes the machine-readable instructions 320 to generate a personalized treatment adoption plan for the individual that is different from the prescribe treatment plan. The personalized treatment adoption plan can be based on the prescribed treatment plan, but includes one or more modifications, additions, subtractions, etc., or any combination thereof.

For example, the machine learning adoption prediction algorithm 330 can establish a threshold for determining the likelihood that the individual will adopt the prescribed treatment plan. In some implementations, it is determined that the likelihood that the individual will adopt the prescribed treatment plan satisfies the first threshold when the likelihood is below 80 percent. In some implementations, the prescribed treatment plan includes a first recommendation for the individual to begin treatment using the respiratory therapy device 530 at a first range of pressures. In some such implementations, the personalize treatment adoption plan (e.g., the modified version of the prescribed treatment plan) includes a second modified recommendation for the individual to begin treatment using the respiratory therapy device 530 at a second range of pressures that is different from the first range of pressures (e.g., where the second range of pressures is relatively lower and/or easier for the individual to receive).

In some implementations, the prescribed treatment plan includes a first recommendation for the individual to begin treatment using a respiratory therapy device 530. In some such implementations, the personalize treatment adoption plan (e.g., the modified version of the prescribed treatment plan) includes a second recommendation for the individual to begin treatment using a mandibular repositioning device and not start on the respiratory therapy device 530.

In some implementations, the prescribed treatment plan includes a first recommendation for the individual to begin treatment using a respiratory therapy device 530. In some such implementations, the personalize treatment adoption plan (e.g., the modified version of the prescribed treatment plan) includes a second recommendation for the individual to begin treatment by interacting with a coaching program (virtual or in-person) that provides tips, facts, information, benefits, challenges, etc. about using the respiratory therapy device 530. In some such implementations, using feedback, the system 100 can gauge the individual's progress from the coaching to determine when to recommend the next step in treatment (e.g., actual use of the respiratory therapy device 530, use of a MRD, etc.).

In some implementations, the prescribed treatment plan includes a first recommendation for the individual to begin treatment using the respiratory therapy device 530 at a first range of pressures. In some such implementations, the personalized treatment adoption plan (e.g., the modified version of the prescribed treatment plan) includes a second recommendation for the individual to begin treatment by having a surgery and not start on the respiratory therapy device 530. In some such implementations, for example, the recommended surgery can include bariatric surgery, oral surgery, liposuction surgery, or any combination thereof.

Oral and maxillofacial surgery (OMFS or OMS) specifically includes surgery of the face, mouth, and jaws. Such OMS procedures can include, for example, dentoalveolar surgery (surgery to remove impacted teeth, difficult tooth extractions, extractions on medically compromised patients, bone grafting or preprosthetic surgery to provide better anatomy for the placement of implants, dentures, or other dental prostheses). Other OMS procedures can include surgery to insert osseointegrated (bone fused) dental implants and maxillofacial implants for attaching craniofacial prostheses and bone anchored hearing aids. Other OMS procedures include cosmetic surgery of the head and neck: (rhytidectomy/facelift, browlift, blepharoplasty/Asian blepharoplasty, otoplasty, rhinoplasty, septoplasty, cheek augmentation, chin augmentation, genioplasty, oculoplastics, neck liposuction, hair transplantation, lip enhancement, injectable cosmetic treatments like botox, fillers, platelet rich plasma, stem cells, chemical peel, mesotherapy). OMS procedures can also include orthognathic surgery, surgical treatment/correction of dentofacial deformity as well as management of facial trauma, and sleep apnea In some implementations, the prescribed treatment plan includes a first recommendation for the individual to begin treatment using the respiratory therapy device 530 at a first range of pressures. In some such implementations, the personalized treatment adoption plan (e.g., the modified version of the prescribed treatment plan) includes a second recommendation for the individual to begin treatment by adopting a diet, adopting an exercise plan, or a combination thereof. For example, a personal trainer can be assigned to create a workout schedule that does not exhaust the individual but enhances their quality of life. For another example, the workout schedule can be conscious to not require the individual to exercise too much, as it might result in a poorer sleep quality (e.g., snoring more). Also, the trainer can assist in training specific muscles to aid in avoiding sleep related breathing issues (e.g., sleep apnea, etc.).

In some implementation, the prescribed treatment plan includes a first recommendation for the individual to begin treatment using a respiration device. In some such implementations, the personalized treatment adoption plan (e.g., the modified version of the prescribed treatment plan) includes a second recommendation for the individual to begin treatment using an adjustable bed-related device. The adjustable bed-related device can aid in addressing positional issues like positional obstructive sleep apnea (OSA), positional snoring, etc. In some implementations, the adjustable bed-related device includes an adjustable pillow, an adjustable mattress, an adjustable bed frame, adjustable bedding, or any combination thereof.

In some implementations, the prescribed treatment plan includes a first recommendation for the individual to begin treatment using the respiratory therapy device 530. In some such implementations, the personalized treatment adoption plan (e.g., the modified version of the prescribed treatment plan) includes a second recommendation for the individual to begin treatment using a nasal strip.

While the above examples of modifications to prescribed treatment plans to form personalized treatment adoption plans are described in a particular order and/or relationship, it is contemplated that the above exemplary modifications can be combined in any order and/or combination to create a personalized treatment adoption plan for an individual.

For example, in some implementations, the prescribed treatment plan includes a first recommendation for the individual to begin treatment using the respiratory therapy device 530. In some such implementations, the personalized treatment adoption plan (e.g., the modified version of the prescribed treatment plan) includes a second recommendation for the individual to begin treatment by using a mandibular repositioning device, having a surgery procedure, losing weight, adopting a diet, adopting an exercise regimen, avoiding or reducing consumption of alcohol, avoiding or reducing consumption of tobacco, quitting smoking, avoiding or reducing caffeine consumption, using a humidifier when sleeping, using a tongue stabilizing device, avoiding or reducing use of sleeping pills, practicing vocal exercises, practicing one or more breathing exercises, using an adjustable bed-related device, or any combination thereof.

In some implementations, the system 100 provides the personalize treatment adoption plan to the individual (e.g., via one or more of the terminal devices 500) before any treatment is implemented for the individual. The modified version of the prescribed treatment plan is provided to the individual based at least in part on the determined likelihood that the individual will adopt the prescribed treatment plan.

In some implementations, the machine learning adoption prediction algorithm 330 is configured to determine that the likelihood the individual will adopt the prescribed treatment plan satisfies a second threshold (e.g., the likelihood is greater than a predetermined amount). Upon such a determination, the generated personalized treatment adoption plan for the individual is the prescribed treatment plan. For example, the likelihood that the individual will adopt the prescribed treatment plan satisfies the second threshold when the likelihood is equal to or greater than 80 percent, greater than 85 percent, greater than 90 percent, greater than 95 percent, etc., or any other percentage likelihood.

In some implementations of the present disclosure, the control system 400 receives user input from an individual via one or more of the terminal devices 500. The user input can be processed using the machine learning adoption prediction algorithm 330. In some implementations, the user input includes one or more videos depicting at least a portion of the individual, one or more images depicting at least a portion of the individual, or a combination thereof.

In some implementations, the machine learning adoption prediction algorithm 330 can process the user input by analyzing the user input to determine a risk of sleeping disorder for the individual. For example, image data of the individual can be analyzed to determine face color, eye data, etc.). Based on this analysis, the machine learning adoption prediction algorithm 330 is configured to predict a risk of sleep apnea for the individual. This calculated risk for sleep apnea can be included in the determined likelihood that the individual will adopt the prescribed treatment plan. For example, if it is determined that the individual is at risk for sleep apnea or actually has sleep apnea, the machine learning adoption prediction algorithm 330 might predict that the individual is more likely to adopt the prescribed treatment plan. Similarly, if the machine learning adoption prediction algorithm 330 determines that the risk for sleep apnea is low, then it might be determined that the individual is less likely to adopt the prescribed treatment plan because they will likely not see benefits or not see significant benefits that are worth the inconvenience of the treatment.

The processing of the user input can alternatively and/or additionally be used to aid in determining an effectiveness of a currently prescribed treatment. Based on the effectiveness or lack of effectiveness, the system 100 can generate one or more modifications to the current treatment plan to aid in increasing the likelihood that the individual continues to adopt and/or comply with the treatment plan for the long term and not quit treatment (e.g., within a month or two).

As discussed in connection with FIG. 1, the system 100 can include the one or more sensors for collecting information. The one or more sensors can include a pressure sensor that outputs pressure data that can be stored in the memory 300 and/or analyzed by the processor 410 of the control system 400. In some implementations, the pressure sensor is an air pressure sensor (e.g., barometric pressure sensor) that generates sensor data indicative of the respiration (e.g., inhaling and/or exhaling) of the user of the respiratory therapy device 530 and/or ambient pressure. The pressure sensor can be, for example, a capacitive sensor, an electromagnetic sensor, a piezoelectric sensor, a strain-gauge sensor, an optical sensor, a potentiometric sensor, or any combination thereof.

The one or more sensors can include a flow rate sensor that outputs flow rate data. In some implementations, the flow rate sensor is used to determine an air flow rate from the respiratory therapy device 530, an air flow rate through a tube of the respiratory therapy device 530, an air flow rate through a mask of the respiratory therapy device 530, or any combination thereof. The flow rate sensor can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The one or more sensors can include a temperature sensor that outputs temperature data. In some implementations, the temperature sensor generates temperatures data indicative of a core body temperature of the individual, a skin temperature of the individual, a temperature of the air flowing from the respiratory therapy device 530, an ambient temperature, or any combination thereof. The temperature sensor can be, for example, a thermocouple sensor, a thermistor sensor, a silicon band gap temperature sensor or semiconductor-based sensor, a resistance temperature detector, or any combination thereof.

The one or more sensors can include a microphone that outputs audio data. The audio data generated by the microphone is reproducible as one or more sound(s) during a sleep session. The audio data form the microphone can also be used to identify (e.g., using the control system 400) an event experienced by the user during the sleep session, as described in further detail herein. The microphone can be coupled to or integrated in any one or more of the terminal devices 500.

The one or more sensors can include a speaker that outputs sound waves that are audible to an individual. The speaker can be used, for example, as an alarm clock or to play an alert or message to the individual (e.g., in response to an event). In some implementations, the speaker can be used to communicate the audio data generated by the microphone. The speaker can be coupled to or integrated in one or more of the terminal devices 500.

The microphone and the speaker can be used as separate devices. In some implementations, the microphone and the speaker can be combined into an acoustic sensor, as described in, for example, WO 2018/050913, which is hereby incorporated by reference herein in its entirety. In such implementations, the speaker generates or emits sound waves at a predetermined interval, and the microphone detects the reflections of the emitted sound waves from the speaker. The sound waves generated or emitted by the speaker have a frequency that is not audible to the human ear (e.g., below 20 Hz or above around 18 kHz) so as not to disturb the individual while asleep. Based at least in part on the data from the microphone and/or the speaker, the control system 400 can determine a location of the individual and/or one or more of the parameters described in herein.

The one or more sensors can include a radio frequency (RF) transmitter that generates and/or emits radio waves having a predetermined frequency and/or a predetermined amplitude (e.g., within a high frequency band, within a low frequency band, long wave signals, short wave signals, etc.). An RF receiver detects the reflections of the radio waves emitted from the RF transmitter, and this data can be analyzed by the control system 400 to determine a location of the individual and/or one or more of the different parameters or measurements described herein. An RF receiver can also be used for wireless communication in the system 100. In some implementations, the RF receiver and RF transmitter are combined as a part of a radio frequency (RF) sensor. In some such implementations, the RF sensor includes a control circuit. The specific format of the RF communication can be WiFi, Bluetooth, or the like.

In some implementations, the RF sensor is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor. The WiFi router and satellites continuously communicate with one another using WiFi signals. The WiFi mesh system can be used to generate motion data based on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The one or more sensors can include a camera that outputs image data reproducible as one or more images (e.g., still images, video images, thermal images, or a combination thereof) that can be stored in the memory 300. The image data from the camera can be used by the control system 400 to determine one or more of the different parameters described herein for predicting adoption of a therapy. For example, the image data from the camera can be used to identify a location of an individual, to determine a time when the individual enters her bed, to determine a time when the individual exits the bed, and to determine whether the individual interacts with the respiratory therapy device 530.

The one or more sensors can include an infrared (IR) sensor that outputs infrared image data reproducible as one or more infrared images (e.g., still images, video images, or both) that can be stored in the memory 300. The infrared data from the IR sensor can be used to determine one or more parameters during a sleep session, including a temperature of the individual and/or movement of the individual. The IR sensor can also be used in conjunction with the camera when measuring the presence, location, and/or movement of the individual. The IR sensor can detect infrared light having a wavelength between about 700 nm and about 1 mm, for example, while the camera can detect visible light having a wavelength between about 380 nm and about 740 nm.

The one or more sensors can include a PPG sensor that outputs physiological data associated with the individual that can be used to determine one or more parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor can be worn by the individual, embedded in clothing and/or fabric that is worn by the individual, embedded in and/or coupled to any one of the terminal devices 500, etc.

The one or more sensors can include an electrocardiogram (ECG) sensor that outputs physiological data associated with electrical activity of the heart of the individual. In some implementations, the ECG sensor includes one or more electrodes that are positioned on or around a portion of the individual during the sleep session. The physiological data from the ECG sensor can be used, for example, to determine one or more of parameters described herein.

The one or more sensors can include an electroencephalography (EEG) sensor outputs physiological data associated with electrical activity of the brain of the user 210. In some implementations, the EEG sensor includes one or more electrodes that are positioned on or around the scalp of the individual during a sleep session. The physiological data from the EEG sensor can be used, for example, to determine a sleep state of the individual at any given time during the sleep session. In some implementations, the EEG sensor can be integrated in any one of the terminal devices 500.

The one or more sensors can include a capacitive sensor, a force sensor, and a strain gauge sensor that output data that can be stored in the memory 300 and used by the control system 400 to determine one or more parameters described herein. An electromyography (EMG) sensor included in the one or more sensors can output physiological data associated with electrical activity produced by one or more muscles. An oxygen sensor included in the one or more sensors can output oxygen data indicative of an oxygen concentration of gas (e.g., in a tube of the respiratory therapy device 530 and/or a mask used with the respiratory therapy device 530). The oxygen sensor can be, for example, an ultrasonic oxygen sensor, an electrical oxygen sensor, a chemical oxygen sensor, an optical oxygen sensor, or any combination thereof. In some implementations, the one or more sensors also include a galvanic skin response (GSR) sensor, a blood flow sensor, a respiration sensor, a pulse sensor, a sphygmomanometer sensor, an oximetry sensor, or any combination thereof.

The one or more sensors can include an analyte sensor that can be used to detect the presence of an analyte in the exhaled breath of the individual. The data output by the analyte sensor can be stored in the memory 300 and used by the control system 400 to determine identity and concentration of any analytes in the breath of the individual, which can be useful in determining whether the individual will adopt a treatment plan. Individuals on certain substances can be veered towards different treatment plans based on adoption success rate of similarly situated individuals. In some implementations, the analyte sensor is positioned near a mouth of the individual to detect analytes in breath exhaled from the individual's mouth. The analyte sensor can be positioned near the nose of the individual to detect analytes in breath exhaled through the user's nose. In some implementations, the analyte sensor is a volatile organic compound (VOC) sensor that can be used to detect carbon-based chemicals or compounds.

The one or more sensors can include a moisture sensor that outputs data that can be stored in the memory 300 and used by the control system 400. The moisture sensor can be used to detect moisture in various areas surrounding the individual (e.g., inside the tube of the respiratory therapy device 530 or the mask used with the respiratory therapy device 530, near the individual's face, etc.). Thus, in some implementations, the moisture sensor can be coupled to or integrated in any one of the terminal devices 500. The moisture sensor can also be used to monitor the humidity of the ambient environment surrounding the individual, for example, the air inside the bedroom.

The one or more sensors can include a Light Detection and Ranging (LiDAR) sensor for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor can measure and map an area extending 5 meters or more away from the sensor. The LiDAR data can be fused with point cloud data estimated by an electromagnetic RADAR sensor, for example. The LiDAR sensor can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

Figure 2:
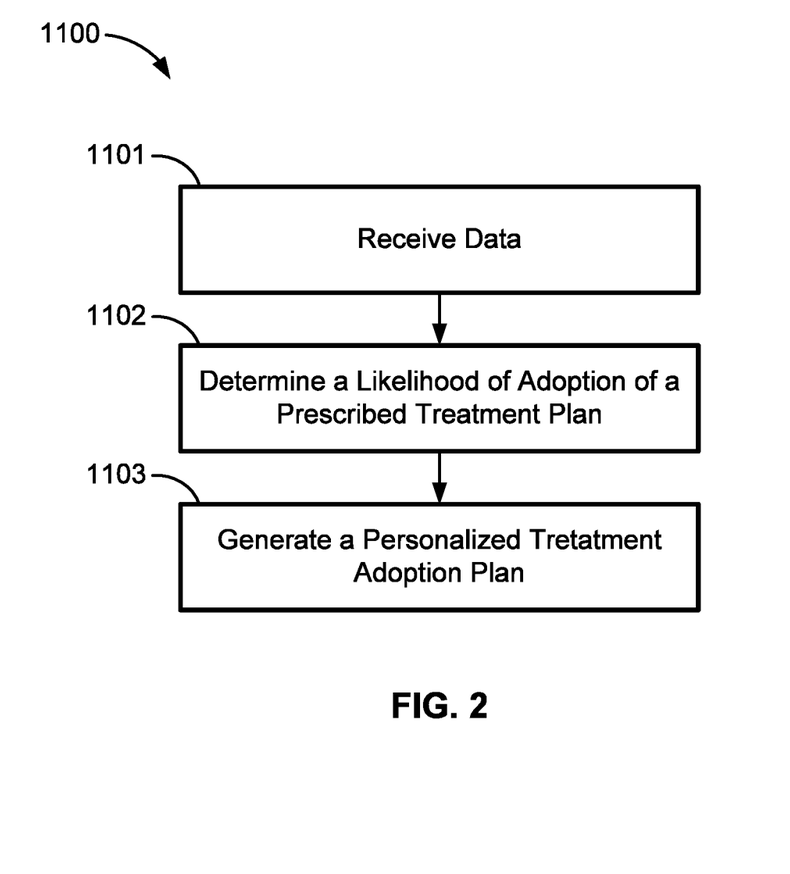
FIG. 2 is a flowchart of a process for predicting a likelihood an individual will adopt a prescribed treatment plan, according to some implementations of the present disclosure.

Referring to FIG. 2, a flow chart for a method 1100 of predicting a likelihood an individual will adopt a prescribed treatment plan is shown. One or more of the steps of the method 1100 described herein can be implemented using the system 100 (FIG. 1). Step 1101 of the method 1100 includes receiving data. The data that is received can be a portion of the data stored in a data repository (e.g., data repository 200). As discussed above, the data can be associated with the individual and/or a plurality of other individuals. At step 1102 of the method 1100, a determination is made of a likelihood that the individual will adopt the prescribed treatment plan. The determination can be made using a machine learning adoption prediction algorithm to process the received data.

At step 1103 of the method 1100, a personalized treatment adoption plan is generated for the individual. The personalized treatment adoption plan can be based on the prescribed treatment plan, but includes one or more modifications, additions, subtractions, etc., or any combination thereof.

Figure 3:
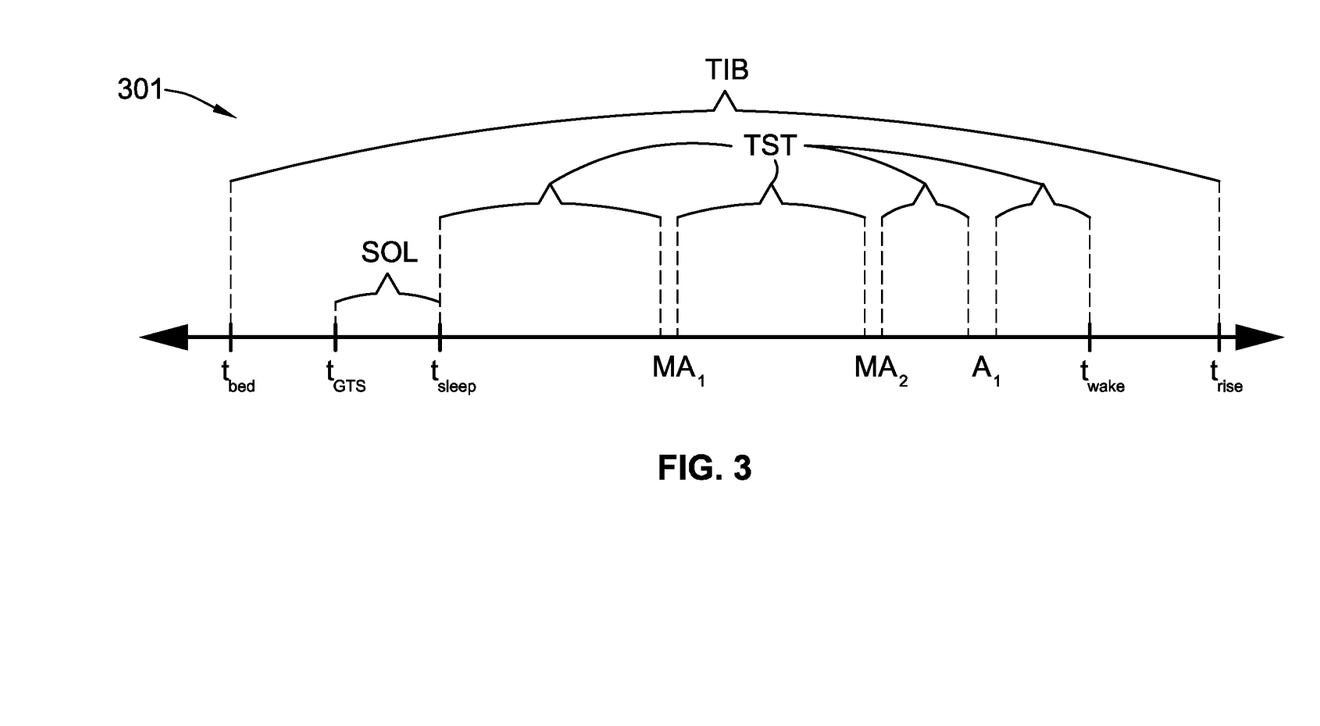
FIG. 3 illustrates an exemplary timeline for a sleep session, according to some implementations of the present disclosure.

As used herein, a sleep session can be defined in a number of ways based on, for example, an initial start time and an end time. Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$ and a second micro-awakening $MA_2$, a wake-up time ($t_{wake}$), and a rising time ($t_{rise}$).

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
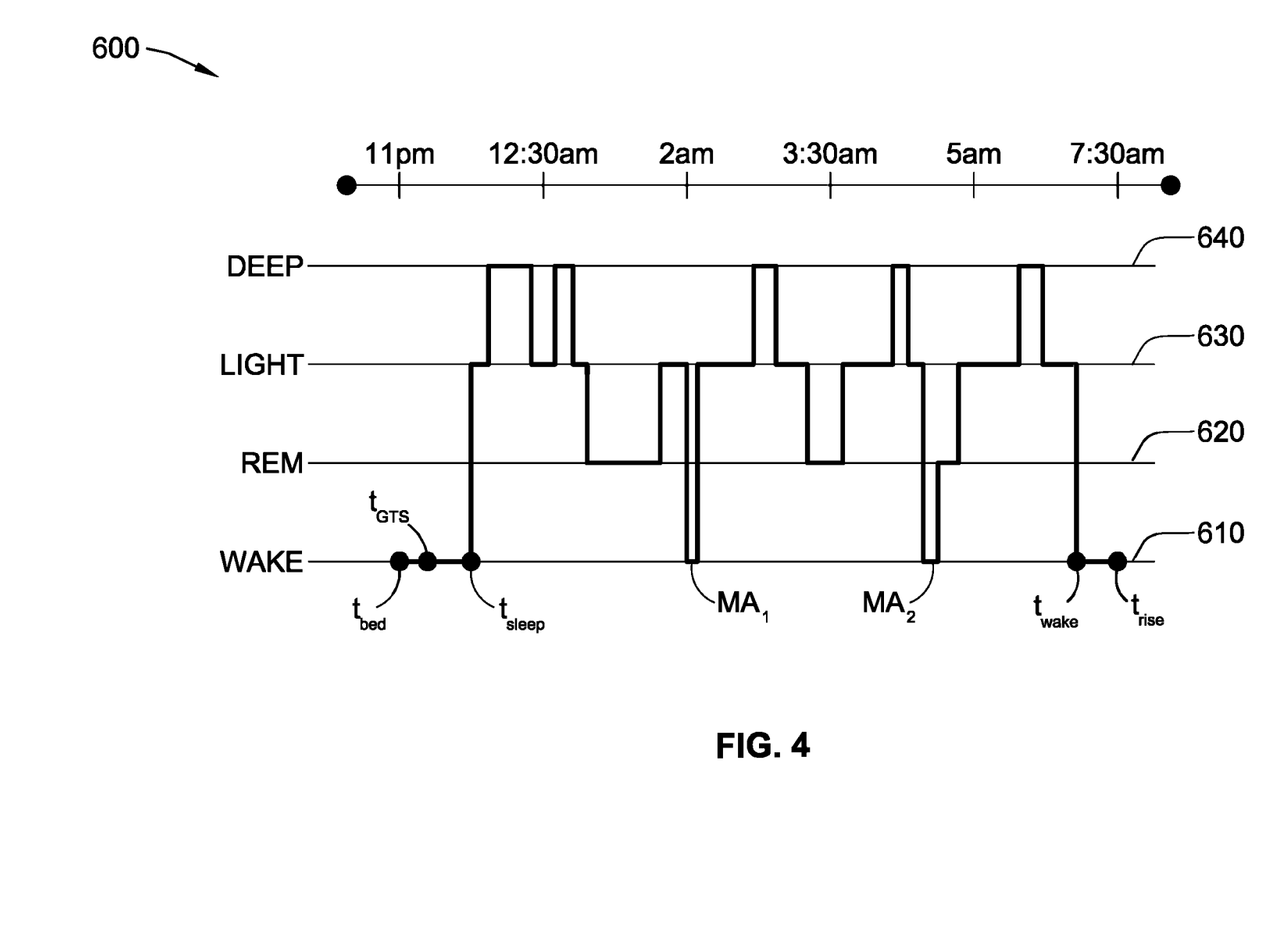
FIG. 4 illustrates an exemplary hypnogram associated with the sleep session of FIG. 3, according to some implementations of the present disclosure.

Referring to FIG. 4, an exemplary hypnogram 600 corresponding to the timeline 301 (FIG. 3), according to some implementations, is illustrated. As shown, the hypnogram 600 includes a sleep-wake signal in bold, a wakefulness stage axis 610, a REM stage axis 620, a light sleep stage axis 630, and a deep sleep stage axis 640. The intersection between the sleep-wake signal and one of the axes 610-640 is indicative of the sleep stage at any given time during the sleep session.

The sleep-wake signal can be generated based on physiological data associated with the user (e.g., generated by one or more of the sensors described herein). The sleep-wake signal can be indicative of one or more sleep states, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 600 is shown in FIG. 4 as including the light sleep stage axis 630 and the deep sleep stage axis 640, in some implementations, the hypnogram 600 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory 300.

The hypnogram 600 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time teed can be determined based on, for example, data generated by the motion sensor, the microphone, the camera, or any combination thereof. The go-to-sleep time can be determined based on, for example, data from the motion sensor (e.g., data indicative of no movement by the user), data from the camera (e.g., data indicative of no movement by the user and/or that the user has turned off the lights) data from the microphone (e.g., data indicative of the using turning off a TV), data from the mobile device 520 (e.g., data indicative of the user no longer using the mobile device 520), data from the pressure sensor and/or the flow rate sensor (e.g., data indicative of the user turning on the respiratory therapy device 530, etc.), or any combination thereof. Data can be generated by the one or more sensors during a sleep session as defined with the help of FIG. 3 or a hypnogram like that of FIG. 4 can be generated to help inform treatment plans for the individual.

One or more elements or aspects or steps, or any portion(s) thereof, from one or more of any of the claims below can be combined with one or more elements or aspects or steps, or any portion(s) thereof, from one or more of any of the other claims below or combinations thereof, to form one or more additional implementations and/or claims of the present disclosure.

While the present disclosure has been described with reference to one or more particular implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:
1. A method comprising:
receiving a prescribed treatment plan for an individual;
receiving data associated with the individual;
using a machine learning adoption prediction algorithm to process at least a portion of the received data to determine a likelihood that the individual will adopt the prescribed treatment plan;

based at least in part on (i) the prescribed treatment plan and (ii) the determined likelihood that the individual will adopt the prescribed treatment plan, generating a personalized treatment adoption plan for the individual;

responsive to implementation, by the individual, of the personalized treatment adoption plan, receiving feedback associated with the personalized treatment adoption plan; and based at least in part on (i) the personalized treatment adoption plan and (ii) the feedback, generating a modified personalized treatment adoption plan.

2. The method of claim 1, wherein responsive to the machine learning adoption prediction algorithm determining that the likelihood the individual will adopt the prescribed treatment plan satisfies a first threshold, the generated personalized treatment adoption plan for the individual includes a modified version of the prescribed treatment plan.

3. The method of claim 2, wherein the likelihood that the individual will adopt the prescribed treatment plan satisfies the first threshold when the likelihood is below 80 percent.

4. The method of claim 2, wherein the prescribed treatment plan includes a first recommendation for the individual to begin treatment using a respiration device at a first range of pressures and the modified version of the prescribed treatment plan includes a second recommendation for the individual to begin treatment using the respiration device at a second range of pressures that is different from the first range of pressures.

5. The method of claim 2, wherein the prescribed treatment plan includes a first recommendation for the individual to begin treatment using a respiration device and the modified version of the prescribed treatment plan includes a second recommendation for the individual to begin treatment using a mandibular repositioning device.

6. The method of claim 2, wherein the prescribed treatment plan includes a first recommendation for the individual to begin treatment using a respiration device at a first range of pressures and the modified version of the prescribed treatment plan includes a second recommendation for the individual to begin treatment by having a surgery, the surgery including bariatric surgery, oral surgery, liposuction surgery, or any combination thereof.

7. The method of claim 2, wherein the prescribed treatment plan includes a first recommendation for the individual to begin treatment using a respiration device at a first range of pressures and the modified version of the prescribed treatment plan includes a second recommendation for the individual to begin treatment by (i) adopting a diet, (ii) adopting an exercise plan, or (iii) or both (i) and (ii).

8. The method of claim 2, wherein the prescribed treatment plan includes a first recommendation for the individual to begin treatment using a respiration device and the modified version of the prescribed treatment plan includes a second recommendation for the individual to begin treatment using an adjustable bed-related device, the adjustable bed-related device including an adjustable pillow, an adjustable mattress, an adjustable bed frame, adjustable bedding, or any combination thereof.

9. The method of claim 2, wherein the prescribed treatment plan includes a first recommendation for the individual to begin treatment using a respiration device and the modified version of the prescribed treatment plan includes a second recommendation for the individual to begin treatment using a nasal strip.

10. The method of claim 2, wherein the prescribed treatment plan includes a first recommendation for the individual to begin treatment using a respiration device and the modified version of the prescribed treatment plan includes a second recommendation for the individual to begin treatment by using a mandibular repositioning device, having a surgery procedure, losing weight, adopting a diet, adopting an exercise regimen, avoiding or reducing consumption of alcohol, avoiding or reducing consumption of tobacco, quitting smoking, avoiding or reducing caffeine consumption, using a humidifier when sleeping, using a tongue stabilizing device, avoiding or reducing use of sleeping pills, practicing vocal exercises, practicing one or more breathing exercises, using an adjustable bed-related device, or any combination thereof.

11. The method of claim 2, wherein responsive to the machine learning adoption prediction algorithm determining that the likelihood the individual will adopt the prescribed treatment plan satisfies a second threshold, the generated personalized treatment adoption plan for the individual is the prescribed treatment plan, and wherein the likelihood that the individual will adopt the prescribed treatment plan satisfies the second threshold when the likelihood is equal to or greater than 80 percent.

12. The method of claim 1, wherein the data associated with the individual includes personal data associated with a plurality of individuals, adherence data associated with a plurality of individuals that are similar to the individual, a summary of at least a portion of historical events that led the individual to a sleep-related diagnosis, an indication of a type of person that provided the individual with a sleep-related diagnosis, a determination of whether the individual encounters difficulties breathing during sleep, relationship information of the individual, web searches performed by the individual, a determination of whether the individual is likely to exhibit binge-like behaviour, a determination of whether the individual is likely to change behaviour, a summary of at least a portion of a historical account of clinical behaviour that the individual has changed, one or more daily health assessments that include the occurrence and frequency of headaches and migraines experiences by the individual, dependent-family information of the individual, subscriptions of the individual in mobile-based or web-based health applications, social media information associated with the individual, support group information related to respiration device usage, a determination of a tendency of the individual to be an early adopter of technology, treatment plans prescribed to the individual, information associated with whether the individual is a drug user, information associated with whether the individual consumes alcohol, or any combination thereof.

13. The method of claim 1, wherein the data includes training data that is associated with a plurality of individuals, the method further comprising:

training the machine learning adoption prediction algorithm with the training data such that the machine learning adoption prediction algorithm is configured to (i) receive as an input the at least a portion of the received data and (ii) determine as an output the likelihood that the individual will adopt the prescribed treatment plan.

14. The method of claim 1, wherein the feedback is associated with (i) a level of compliance of the individual with the personalized treatment plan, (ii) answers to one or more questions by the individual, (iii) sensor data, or (iv) any combination thereof.

15. The method of claim 1, further comprising:

causing a notification to be provided to a terminal device based on the generated personalized treatment adoption plan for the individual, the terminal device including a personal computer, a mobile device, a respiratory therapy device, or any combination thereof, wherein the notification includes a command to adjust a setting on the respiratory therapy device based at least in part on the personalized treatment adoption plan.

16. The method of claim 1, wherein the data is stored in a data repository communicatively coupled to a network and including a plurality of storage devices, the plurality of storage devices including a social media database, an electronic healthcare record database, a wearable technology database, or any combination thereof.

17. The method of claim 1, further comprising:
receiving user input from the individual, wherein the using the machine learning adoption prediction algorithm includes analysing the user input to determine a risk of sleeping disorder for the individual, and wherein the user input includes one or more videos depicting at least a portion of the individual, one or more images depicting at least a portion of the individual, or a combination thereof.

18. A system for predicting adoption of a prescribed treatment plan by an individual, the system comprising:
a data repository communicatively coupled to a network and including a plurality of storage devices storing data;
a memory storing machine-readable instructions and a machine learning adoption prediction algorithm; and
a control system including one or more processors configured to execute the machine-readable instructions to:
receive the prescribed treatment plan for the individual;
receive at least a portion of the data stored in the data repository, the at least a portion of the data being associated with the individual;
use the machine learning adoption prediction algorithm to process the received at least a portion of the data to determine a likelihood that the individual will adopt the prescribed treatment plan; and
based at least in part on (i) the prescribed treatment plan and (ii) the determined likelihood that the individual will adopt the prescribed treatment plan, generate a personalized treatment adoption plan for the individual;
responsive to implementation, by the individual, of the personalized treatment adoption plan, receive feedback associated with the personalized treatment adoption plan; and
based at least in part on (i) the personalized treatment adoption plan and (ii) the feedback, generate a modified personalized treatment adoption plan.

19. The system of claim 18, wherein responsive to the machine learning adoption prediction algorithm determining that the likelihood the individual will adopt the prescribed treatment plan satisfies a first threshold, the generated personalized treatment adoption plan for the individual includes a modified version of the prescribed treatment plan.

20. The system of claim 19, wherein the prescribed treatment plan includes a first recommendation for the individual to begin treatment using a respiration device and the modified version of the prescribed treatment plan includes a second recommendation for the individual to begin treatment by using a mandibular repositioning device, having a surgery procedure, losing weight, adopting a diet, adopting an exercise regimen, avoiding or reducing consumption of alcohol, avoiding or reducing consumption of tobacco, quitting smoking, avoiding or reducing caffeine consumption, using a humidifier when sleeping, using a tongue stabilizing device, avoiding or reducing use of sleeping pills, practicing vocal exercises, practicing one or more breathing exercises, using an adjustable bed-related device, begin using a nasal strip, or any combination thereof.

21. The system of claim 18, further comprising a terminal device associated with the individual and configured to receive a notification from the control system based on the generated personalized treatment adoption plan for the individual, the terminal device including a personal computer, a mobile device, a respiratory therapy device, or any combination thereof, and the notification including a command to adjust a setting on the respiratory therapy device based at least in part on the personalized treatment adoption plan.

22. The system of claim 18, wherein the plurality of storage devices includes a social media database, an electronic healthcare record database, a wearable technology database, or any combination thereof.

23. The system of claim 18, wherein the data associated with the individual includes personal data associated with a plurality of individuals, adherence data associated with a plurality of individuals that are similar to the individual, a summary of at least a portion of historical events that led the individual to a sleep-related diagnosis, an indication of a type of person that provided the individual with a sleep-related diagnosis, a determination of whether the individual encounters difficulties breathing during sleep, relationship information of the individual, web searches performed by the individual, a determination of whether the individual is likely to exhibit binge-like behaviour, a determination of whether the individual is likely to change behaviour, a summary of at least a portion of a historical account of clinical behaviour that the individual has changed, one or more daily health assessments that include the occurrence and frequency of headaches and migraines experiences by the individual, dependent-family information of the individual, subscriptions of the individual in mobile-based or web-based health applications, social media information associated with the individual, support group information related to respiration device usage, a determination of a tendency of the individual to be an early adopter of technology, treatment plans prescribed to the individual, information associated with whether the individual is a drug user, information associated with whether the individual consumes alcohol, or any combination thereof.

24. The system of claim 18, wherein the data includes training data that is associated with a plurality of individuals; and
wherein the machine learning adoption prediction algorithm is trained with the training data such that the machine learning adoption prediction algorithm is configured to (i) receive as an input the at least a portion of the data and (ii) determine as an output the likelihood that the individual will adopt the prescribed treatment plan.

25. The system of claim 18, wherein the feedback is associated with (i) a level of compliance of the individual with the personalized treatment plan, (ii) answers to one or more questions by the individual, (iii) sensor data, or (iv) any combination thereof.

* * * * *